United States Patent [19]

Franklin et al.

[11] Patent Number: 4,968,850

[45] Date of Patent: Nov. 6, 1990

[54] PROCESS FOR THE MANUFACTURE OF A FLUORINATED HYDROCARBON

[75] Inventors: James Franklin, Brussels; Francine Janssens, Vilvoorde, both of Belgium

[73] Assignee: Solvay & Cie (Société Anonyme), Brussels, Belgium

[21] Appl. No.: 404,910

[22] Filed: Sep. 8, 1989

[30] Foreign Application Priority Data

Sep. 26, 1988 [FR] France .................... 88 12643

[51] Int. Cl.$^5$ .............................................. C07C 17/08
[52] U.S. Cl. .................................................... 570/166
[58] Field of Search ...................... 570/165, 166, 168

[56] References Cited

U.S. PATENT DOCUMENTS 4,766,258  8/1988  Komatsu et al. .................... 570/168

FOREIGN PATENT DOCUMENTS

| | | |
|---|---|---|
| 858768 | 3/1978 | Belgium . |
| 0187643 | 7/1986 | European Pat. Off. . |
| 1814340 | 8/1969 | Fed. Rep. of Germany . |
| 1036233 | 2/1986 | Japan . |
| 979271 | 1/1965 | United Kingdom . |
| 1556131 | 11/1979 | United Kingdom . |

*Primary Examiner*—Alan Siegel
*Attorney, Agent, or Firm*—Spencer & Frank

[57] ABSTRACT

The invention relates to a process for the manufacture of a fluorinated hydrocarbon by the reaction of hydrogen fluoride with an unsaturated chlorinated hydrocarbon in the liquid phase in the presence of a catalyst constituted by a tin compound and of an additive constituted by an organophosphorus compound.

8 Claims, No Drawings

PROCESS FOR THE MANUFACTURE OF A FLUORINATED HYDROCARBON

The present invention relates to a process for the manufacture of a fluorinated hydrocarbon by the reaction of hydrogen fluoride with an unsaturated chlorinated hydrocarbon in the presence of a tin compound and an organophosphorus compound.

The process for the manufacture of 1-chloro-1,1-difluoroethane by the reaction of hydrogen fluoride with vinylidene chloride in the presence of a tin compound such as tin tetrachloride is known in particular from Belgian Patent 858,768 in the name of Solvay & Co.

In addition, European Patent Application EP 0,187,643 divulges, in a general manner, processes for the manufacture of fluorinated hydrocarbons from chlorinated hydrocarbons by reaction with hydrogen fluoride in the presence of a tin compound and an additive chosen from compounds containing oxygen or nitrogen; among the latter, water, hydrogen peroxide, oxygen-containing organic compounds such as alcohols, ketones, carboxylic acids, aldehydes, ethers, esters and epoxy compounds, ammonia ($NH_3$) and nitrogen-containing organic compounds such as pyridine and amines are mentioned in particular.

The additives known in the prior art have, however, low stability in the reaction medium and/or reduce the activity of the tin compound when they are used in the presence of hydrogen fluoride and a chlorinated compound such as vinylidene chloride, which compromises the efficiency of these processes.

The invention itself relates to a process for the manufacture of a fluorinated hydrocarbon with the aid of an additive which no longer has these disadvantages. In fact a process has been found which has good efficiency and in which the activity of the catalyst used is increased and/or the stability of the additives is improved, and in which few oligomers are formed and the selectivity for worthwhile products is high, which is accompanied by a reduction of pollution from the effluents. In addition, when the reaction is carried out in a continuous reactor, the rate of purging the liquid reaction medium is reduced, which therefore limits the losses of hydrogen fluoride and catalyst. In addition, because of the absence of water or of compounds which generate this product, a clear reduction in corrosion of the reactor is observed since there is no formation of aqueous hydrochloric acid.

For this purpose the invention relates to a process for the manufacture of a fluorinated hydrocarbon by the reaction of hydrogen fluoride with an unsaturated chlorinated hydrocarbon in the liquid phase in the presence of a catalyst constituted by a tin compound and of an additive constituted by an organophosphorus compound.

The organophosphorus compound used in the process of the invention is generally chosen from the organic phosphites, phosphines or phosphates. It normally corresponds to general formulae (A) or (B):

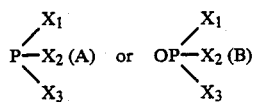

in which
P represents the element phosphorus,
0 the element oxygen
and $X_1$, $X_2$ and $X_3$ represent, independently of each other, organic or inorganic radicals which may be identical or different, at least one of radicals $X_1$, $X_2$ or $X_3$ being an organic radical.

Normally $X_1$, $X_2$ and $X_3$ represent the radicals OR or R, in which R represents hydrogen, a halogen, a saturated substituted or unsubstituted linear or branched aliphatic group having from 1 to 12 carbon atoms, or a substituted or unsubstituted aromatic group having from 5 to 10 carbon atoms.

Advantageously, R represents a halogen such as chlorine, a saturated unsubstituted linear or branched aliphatic group having from 1 to 8 carbon atoms or a substituted or unsubstituted aromatic group having at least 6, and preferably 6 to 8, carbon atoms.

Preferably, R represents chlorine, a saturated unsubstituted linear or branched aliphatic group having from 1 to 5 carbon atoms or a phenyl group.

In a particularly preferred manner, the organophosphorus compound used is chosen from triethyl phosphite, trimethyl phosphite, tri-n-butyl phosphite, triisopropyl phosphite, diethyl phosphite, tri-n-butylphosphine, triphenylphosphine, chlorodiphenylphosphine and triphenylphosphine oxide.

Good results have been obtained with triethyl phosphite, trimethyl phosphite, tri-n-butyl phosphite, triisopropyl phosphite, chlorodiphenylphosphine and triphenylphosphine oxide. Very good results have been obtained with triethyl phosphite.

The process according to the invention makes use of a catalyst constituted by a tin compound. Halides, such as chlorides and fluorides, oxides and oxyhalides, and preferably tin chlorides and fluorides, are preferably used as tin compound. Tin tetrachloride has been shown to be particularly worthwhile.

The quantity of organophosphorus additive used in the process according to the invention is generally between 0.01 and 5 moles per mole of catalyst. Preferably, the operation is carried out between 0.05 and 3 moles of additive per mole of catalyst, and, in a particularly preferred manner, between 0.1 and 2 moles of additive Per mole of catalyst.

The quantity of catalyst present in the process can vary between wide limits. It generally corresponds to a weight of between 0.1 and 30% of that of the reaction medium, and preferably between 0.5 and 15% of the weight of the latter.

The quantity of hydrogen fluoride used in the process can also vary between wide limits. It is generally between 1 and 5 moles per mole of chlorinated hydrocarbon, and preferably between 1.5 and 4 moles of chlorinated hydrocarbon used.

The temperature at which the reaction is carried out is generally between 30 and 180° C, and preferably between 40 and 120° C. The pressure at which the reaction is carried out is chosen so as to maintain the reaction medium in the liquid form. It is most often between 2 and 50 bars, and varies with the temperature of the reaction medium.

The process according to the invention is applied to the manufacture of any fluorinated or chlorofluorinated hydrocarbon from the corresponding unsaturated chlorinated hydrocarbon, and in particular to the manufacture of 1,1-dichloro-1-fluoroethane and of 1-chloro-1,1-difluoroethane from vinylidene chloride.

The process of the invention can be carried out in any reactor or apparatus which allows the conditions described above to be collected together. The process can be carried out batchwise or continuously.

The organophosphorus additive can be used in various manners, thus it can be introduced as such into the reactor before the reaction, or can be dissolved in the chlorinated hydrocarbon or introduced concomitantly with the latter, or be dissolved in an intermediate product of the reaction.

In the case of the reaction from vinylidene chloride in the presence of triethylphosphite, good results have been obtained following the introduction of the additive as such into the reactor before the reaction and following the introduction of the additive dissolved in the vinylidene chloride.

The following examples illustrate the invention.

EXAMPLE 1

A 0.5 l autoclave provided with a safety valve, a system for introducing the reagents, a means for taking liquid samples, a manometer, a stirrer and a sampling system constituted by a bubbler followed by a water reservoir is used.

0.05 mol of triethyl phosphite is introduced into this autoclave.

A vacuum (about 20 mm Hg) is drawn on the autoclave and it is cooled to $-40°C$. by immersing it in an ethanol/$CO_2$ mixture. Then 1 mol of vinylidene chloride is introduced into the autoclave by aspiration.

0.05 mol of tin tetrachloride are then introduced, and immediately after 3 mol of hydrogen fluoride.

The autoclave is heated to 60 °C., and the temperature of the reaction medium is maintained constant at 60°C. throughout the reaction.

The evolution of pressure is followed during time, until it reaches 17.5 bars absolute.

The autoclave is then quickly cooled to $-20C$.
The reaction has lasted 5.5 hours.
The conversion rate of the vinylidene chloride (VC2) in 98.5%

$$\left( \text{conversion rate} = \frac{\text{starting } VC2 \text{ in mol} - \text{finishing } VC2 \text{ in mol}}{\text{starting } VC2 \text{ in mol}} \right).$$

The analysis of all the products obtained is given in Table 1 below.

$$\left( \text{Selectivity} = \frac{\text{product measured in mol}}{\text{sum of the products measured in mol}} \right).$$

TABLE 1

| Products obtained: selectivity | | |
| --- | --- | --- |
| 1,1,1-trifluoroethane | | 0.1 |
| 1-chloro-1,1-difluoroethane | | 33.5 |
| 1,1-dichloro-1-fluoroethane | | 61.1 |
| 1,1,1-trichloroethane | mol % | 4.9 |
| oligomers (expressed loss as of starting VC2) | % | 0.37 |

EXAMPLE 2R

The experiment is carried out under conditions identical to those in Example 1, but without adding triethyl phosphite or any other additive to the reaction medium.

The reaction lasted 5 hours.
The conversion rate of the vinylidene chloride is 99.3 %.
The analysis of all the products obtained is given in Table 2 below.

TABLE 2

| Products obtained: selectivity | | |
| --- | --- | --- |
| 1,1,1-trifluoroethane | | 1.5 |
| 1-chloro-1,1-difluoroethane | | 39.6 |
| 1,1-dichloro-1-fluoroethane | | 54.7 |
| 1,1,1-trichloroethane | mol % | 3.2 |
| oligomers (expressed as loss of starting VC2) | % | 0.87 |

Comparison of Examples 1 and 2R shows that the effect of the addition of triethyl phosphite is to reduce the formation of oligomers in an advantageous manner.

EXAMPLES 3 AND 4

Example 1 is repeated, but using as additive 0.01 mol of triethyl phosphite for Example 3 and 0.025 mol of triethyl phosphite for Example 4.

The analysis of all the results obtained is given in Table 3 below.

TABLE 3

| Products obtained: selectivity | | Example 3 | Example 4 |
| --- | --- | --- | --- |
| 1,1,1-trifluoroethane | | 1.2 | 0.1 |
| 1-chloro-1,1-difluoroethane | | 42.7 | 41.3 |
| 1,1-dichloro-1-fluoroethane | | 51.8 | 53.8 |
| 1,1,1-trichloroethane | mol % | 3.7 | 4.4 |
| oligomers (expressed as loss of starting VC2) | % | 0.47 | 0.30 |
| reaction time | hours | 3.5 | 2.5 |
| conversion rate of vinylidene chloride | mol % | 99.8 | 99.0 |
| activity of the catalyst | | increase | strong increase |

Examples 3 and 4 show that small quantities of triethyl phosphite are sufficient to reduce the manufacture of oligomers.

EXAMPLES 5 AND 6

Example 1 is repeated, but using as additive 0.05 mol of trimethyl phosphite for Example 5 and 0.05 mol of tri-n-butyl phosphite for Example 6.

The analysis of all the results obtained is given in Table 4 below.

TABLE 4

| Products obtained: selectivity | | Example 5 | Example 6 |
| --- | --- | --- | --- |
| 1,1,1-trifluoroethane | | <0.1 | <0.1 |
| 1-chloro-1,1-difluoroethane | | 29.1 | 38.3 |
| 1,1-dichloro-1-fluoroethane | | 65.2 | 56.9 |
| 1,1,1-trichloroethane | mol % | 5.1 | 4.2 |
| oligomers (expressed as loss of starting VC2) | % | 0.45 | 0.55 |
| reaction time | hours | 3 | 5.75 |
| conversion rate of vinylidene chloride | mol % | 99.1 | 99.5 |
| activity of the catalyst | | increase | unchanged |

EXAMPLES 7 AND 8

Example 1 is repeated, but using as additive 0.05 mol of triphenylphosphine oxide for Example 7 and 0.05 mol of chlorodiphenylphosphine for Example 8.

The analysis of all the results obtained is given in Table 5 below.

TABLE 5

| Products obtained: selectivity | | Example 7 | Example 8 |
|---|---|---|---|
| 1,1,1-trifluoroethane | | 0.6 | 0.5 |
| 1-chloro-1,1-difluoroethane | | 39.7 | 40.8 |
| 1,1-dichloro-1-fluoroethane | | 54.8 | 54.1 |
| 1,1,1-trichloroethane | mol % | 4.5 | 4.2 |
| oligomers (expressed as loss of starting VC2) | % | 0.36 | 0.35 |
| reaction time | hours | 5.25 | 5.50 |
| conversion rate of vinylidene chloride | mol % | 99.6 | 99.7 |
| activity of the catalyst | | unchanged | unchanged |

Examples 5, 6, 7 and 8 show that different organophosphorus compounds can be used in an advantageous manner.

EXAMPLE 9R

Example 1 is repeated, but using as additive 0.05 mol of methyl ethyl ketone.

The reaction lasted 3.75 hours.

The conversion rate of vinylidene chloride is 99.2%.

The analysis of all the products obtained is given in Table 6 below.

TABLE 6

| Products obtained: selectivity | | |
|---|---|---|
| 1,1,1-trifluoroethane | | 0.7 |
| 1-chloro-1,1-difluoroethane | | 39.7 |
| 1,1-dichloro-1-fluoroethane | | 54.3 |
| 1,1,1-trichloroethane | mol % | 4.5 |
| oligomers (expressed as loss of starting VC2) | % | 0.68 |

Comparison of Examples 2R and 9R shows that the addition of methyl ethyl ketone only leads to a very small reduction in the conversion rate of the oligomers.

In addition, methyl ethyl ketone is unstable in the medium and leads to the formation of undesirable by-products.

What is claimed is:

1. Process for the manufacture of a fluorinated hydrocarbon by the reaction of hydrogen fluoride with an unsaturated chlorinated hydrocarbon in the liquid phase in the presence of a catalyst constituted by a tin compound and of an additive characterized in that the additive is an organophosphorus compound.

2. Process according to claim 1, characterized in that the organophosphorus compound is an organic phosphite, phosphine or phosphate.

3. Process according to claim 2, characterized in that the organophosphorus compound corresponds to general formulae (A) or (B):

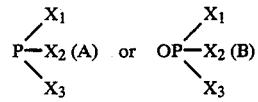

in which

P represents the element phosphorus,

O the element oxygen and $X_1$, $X_2$ and $X_3$ represent, independently of each other, organic or inorganic radicals which may be identical or different, at least one of radicals $X_1$, $X_2$ or $X_3$ being an organic radical.

4. The process according to claim 3, characterized in that $X_1$, $X_2$ and $X_3$ represent the radicals OR or R, in which R represents hydrogen, a halogen, a saturated substituted or unsubstituted linear or branched aliphatic group having from 1 to 12 carbon atoms, or a substituted or unsubstituted aromatic group having from 5 to 10 carbon atoms.

5. The process according to claim 4, characterized in that the organophosphorus compound used is triethyl phosphite.

6. The process according to claim 1, characterized in that from 0.01 to 5 moles of additive are used per mole of catalyst.

7. The process according to claim 1, characterized in that the catalyst used is tin tetrachloride.

8. The process according to claim 1, characterized in that the chlorinated hydrocarbon used is vinylidene chloride.

* * * * *